US00PP30213P2

(12) United States Plant Patent
Weber

(10) Patent No.: US PP30,213 P2
(45) Date of Patent: Feb. 19, 2019

(54) STRAWBERRY PLANT NAMED 'ARCHER'

(50) Latin Name: ***Fragaria* x *ananassa Duch.***
Varietal Denomination: Archer

(71) Applicant: Cornell University, Ithaca, NY (US)

(72) Inventor: Courtney A. Weber, Geneva, NY (US)

(73) Assignee: Cornell University, Ithaca, NY (US)

( * ) Notice: Subject to any disclaimer, the term of this patent is extended or adjusted under 35 U.S.C. 154(b) by 0 days.

(21) Appl. No.: 15/731,949

(22) Filed: Aug. 31, 2017

(51) Int. Cl.
*A01H 5/08* (2018.01)

(52) U.S. Cl.
USPC ..... Plt./208

(58) Field of Classification Search
USPC ..... Plt./208
See application file for complete search history.

*Primary Examiner* — Annette H Para
(74) *Attorney, Agent, or Firm* — LeClairRyan PLLC

(57) ABSTRACT

This invention relates to a new and distinct June-bearing (short day responsive) strawberry plant named 'Archer' primarily adapted to the growing conditions of the west central New York and other regions of similar climate. The plant is botanically known as *Fragaria* x *ananassa* Duch. The new plant is primarily characterized by strong vigor, longer than broad fruit, wide rounded conical fruit shape, very large primary fruit with a prominent internal cavity, uniformly large secondary and tertiary fruit, uniformity in shape between primary, secondary fruit and tertiary fruit, reflexed calyx, and intense red fruit color externally and internally.

7 Drawing Sheets

Figure 1A:
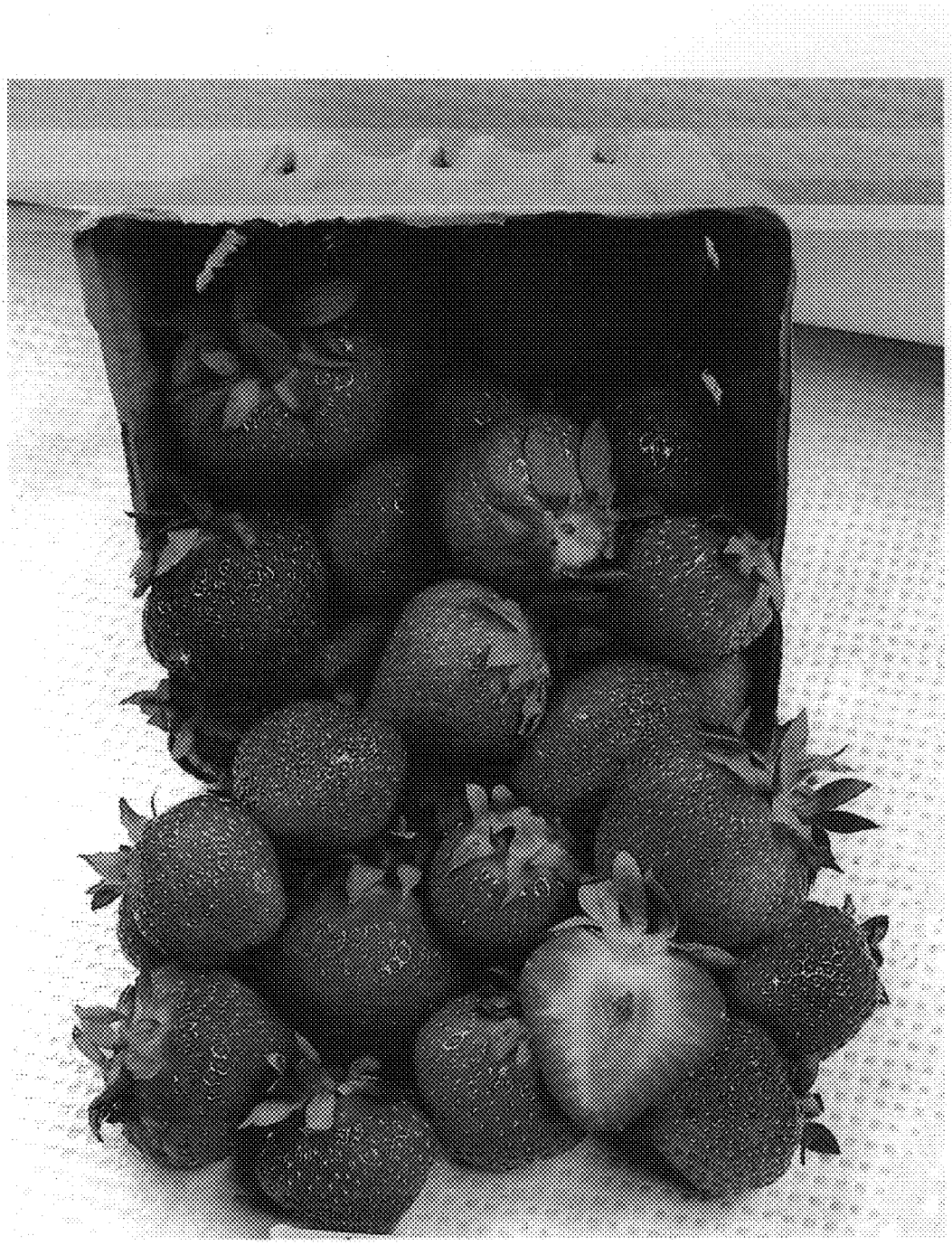

This invention was made with government support under grant number NYG-632421 awarded by the USDA. The government has certain rights in this invention.

FIELD OF THE INVENTION

The present invention relates to a new and distinct June-bearing (short day responsive) strawberry plant designated as 'Archer'. The plant is botanically known as *Fragaria* x *ananassa* Duch.

BACKGROUND OF THE INVENTION

The new and distinct plant of strawberry originated from a hand-pollinated hybridization made in 1997 in Geneva, N.Y. between the Cornell University Selection NY1786 (not patented) x 'L'Amour' (U.S. Plant Pat. No. 16,480P3). NY1786 is June-bearing with very large average fruit size similar to 'Archer' that is darker red, firm fleshed, and blocky round shaped that ripens in a later season than 'Archer'. 'L'Amour' is June-bearing with smaller average fruit size that is bright red, conic shaped, moderately firm fleshed, and ripens at a similar time as 'Archer'.

Both parents of 'Archer' are hybrids of the strawberry genus of the species *Fragaria* x *ananassa*. Thus 'Archer' is of the species *Fragaria* x *ananassa*.

The seeds resulting from this controlled hybridization were germinated in a greenhouse during the winter of 1999-2000. The resulting seedlings were planted in the spring of 2000 in a field in Geneva, N.Y. and produced fruit in the summer of 2001. One plant, designated NY01-16, was selected for its early ripening, very large fruit with an intense red color, a strong strawberry flavor, and moderately firm flesh. This new plant was discovered by the inventor.

During 2001, the original plant selection (NY01-16) was propagated asexually by stolons (runners) at Geneva, N.Y. and a test planting of ten plants was established. Subsequently, larger test plantings were established with asexually multiplied plants at Geneva, N.Y. The new plant was then tested over several years in the fruiting fields at Geneva, N.Y.

Further propagation was done using tissue culture to produce disease free material for use in further testing. Tissue culture plants were used as mother plants for propagation from stolons. This propagation has demonstrated that the combination of traits disclosed herein as characterizing the new plant are fixed and remain true to type through successive generations of asexual reproduction. All propagules of 'Archer' have been observed to be true to type in that during all asexual multiplication, the vegetative and fruit characteristics of the original plant have been maintained.

All plants planted from dormant crowns or rooted runner tips have fruited after one season of growth in the field.

SUMMARY OF THE INVENTION

The following traits define the new plant as a unique plant, distinguishing it from other commercial varieties in the region.

Medium height plants with an upright growth habit and strong vigor.

Predominantly trifoliate leaves with 4 and 5 leaflet leaves uncommonly present with high leaf gloss and broadly elliptical to obovate leaflets with greater length than width.

Very large primary fruit that is longer than broad, with a tapering rounded to wedge fruit shape, becoming more uniformly conic shaped in secondary and tertiary fruit as well as more evenly long and broad.

Intense red fruit color, red flesh color with a ring of pale flesh surrounding a large cavity in primary and secondary fruit, high fruit aroma, and moderate flesh firmness.

A moderately reflexed calyx generally equal or smaller in diameter than the fruit width.

Medium sized stipule, often highly pigmented on young leaf petioles.

Early mid-season production with high yields.

An extended harvest season compared to other short day responsive types grown in the region.

BRIEF DESCRIPTIONS OF THE DRAWINGS

The patent or application file contains at least one drawing executed in color. Copies of this patent or patent application publication with color drawing(s) will be provided by the Office upon request and payment of the necessary fee. The accompanying color photographs show typical specimens of the new plant at various stages of development as nearly true as it is possible to make in color reproductions. The depicted plant and plant parts were from the first harvest season, approximately 13 months after planting.

Figure 1B:
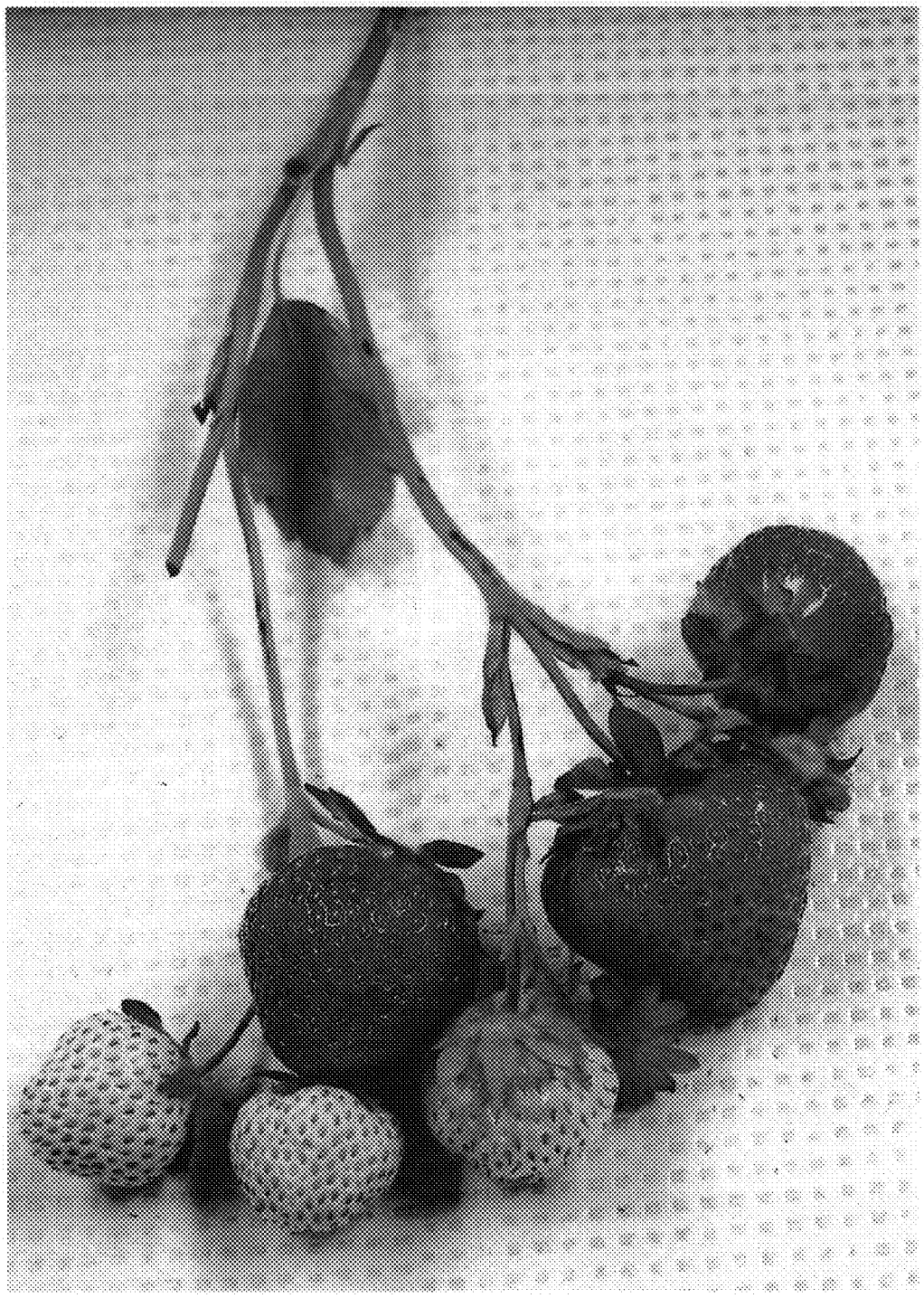

FIGS. 1A-B show typical fruit shape and uniformity (FIG. 1A) and fruiting truss arrangement including large single peduncle bract (FIG. 1B) of 'Archer'.

Figure 2A:
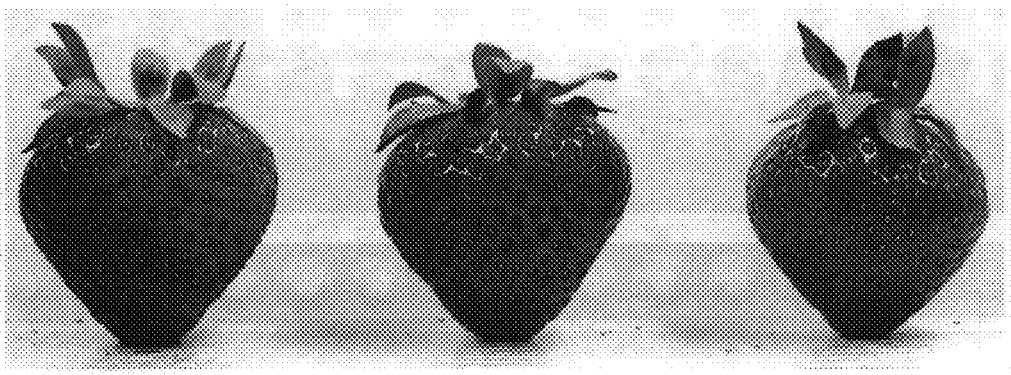
Figure 2B:
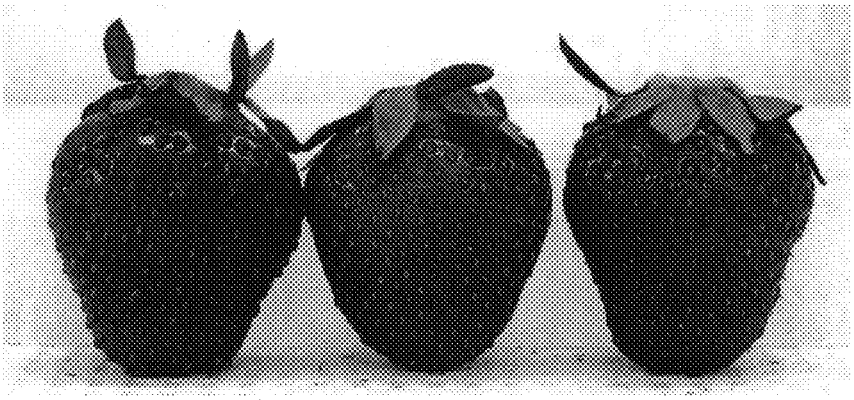
Figure 2C:
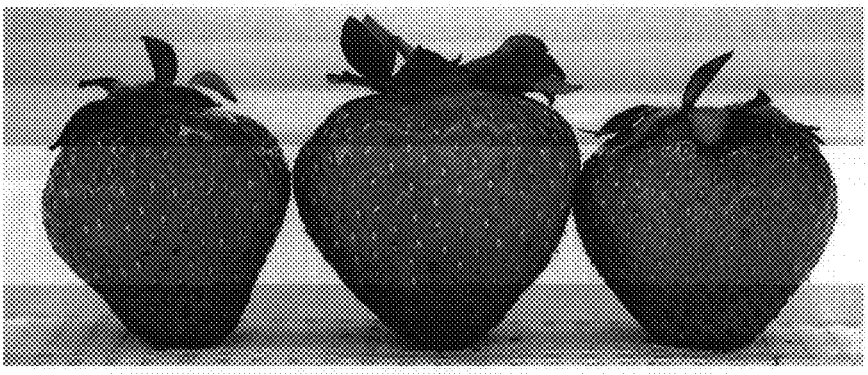

FIGS. 2A-C show typical external fruit characteristics of 'Archer' (FIG. 2A) including calyx structure and fruit shape compared to 'Jewel' (FIG. 2B) and 'Clancy' (FIG. 2C).

Figure 3A:
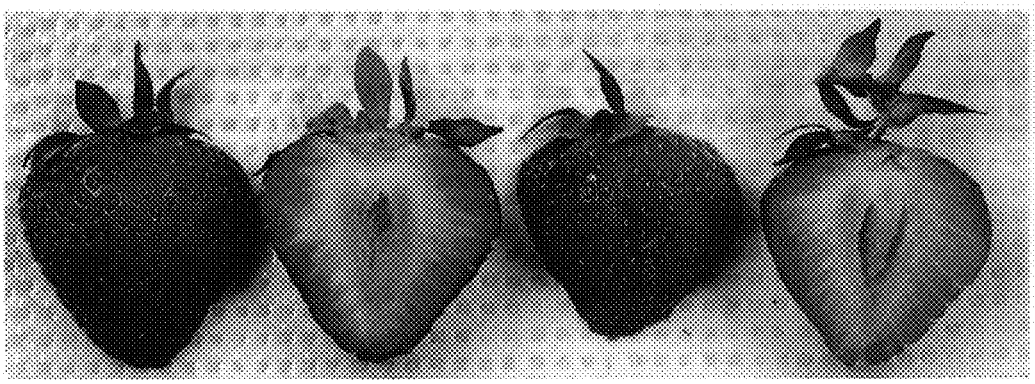
Figure 3B:
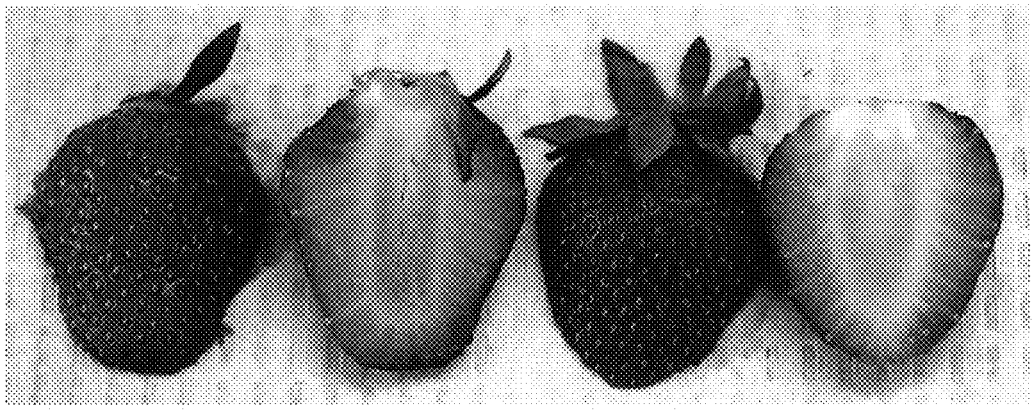
Figure 3C:
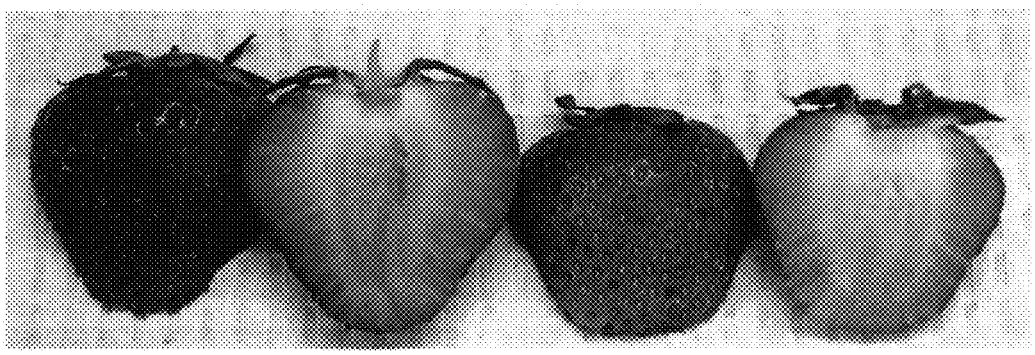

FIGS. 3A-C show typical internal fruit characteristics of 'Archer' (FIG. 3A) compared to 'Jewel' (FIG. 3B) and 'Clancy' (FIG. 3C).

Figure 4A:
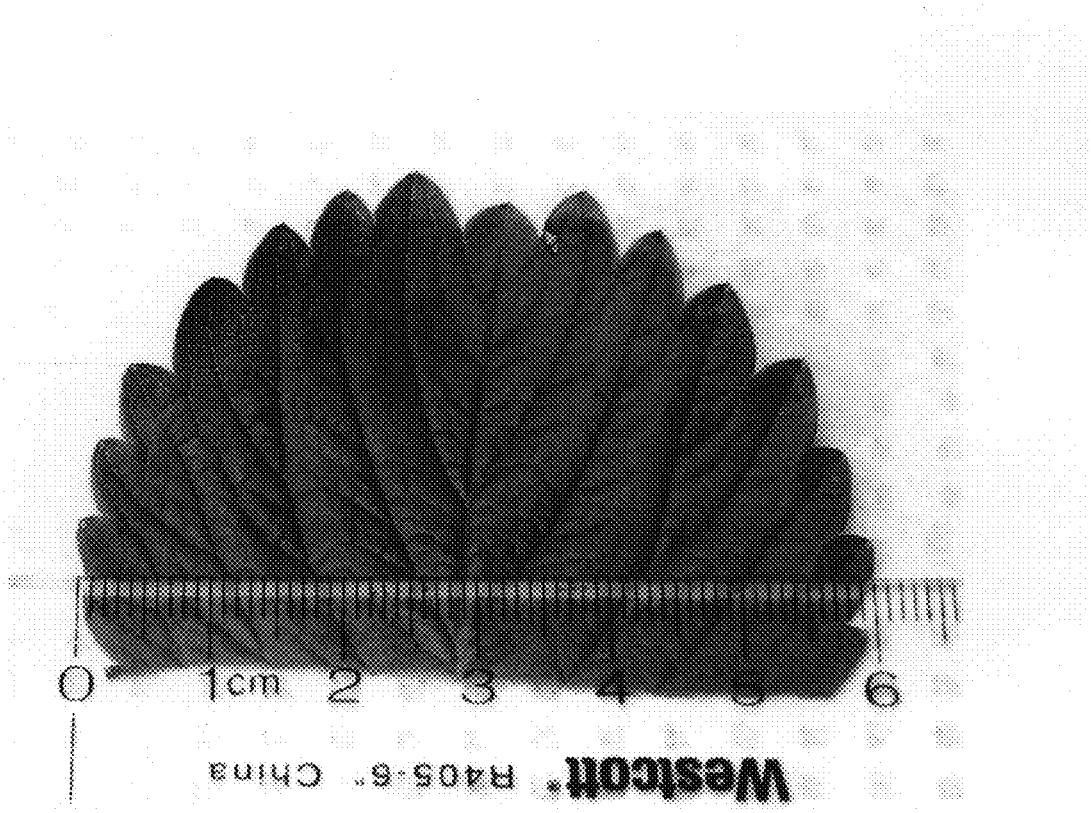
Figure 4B:
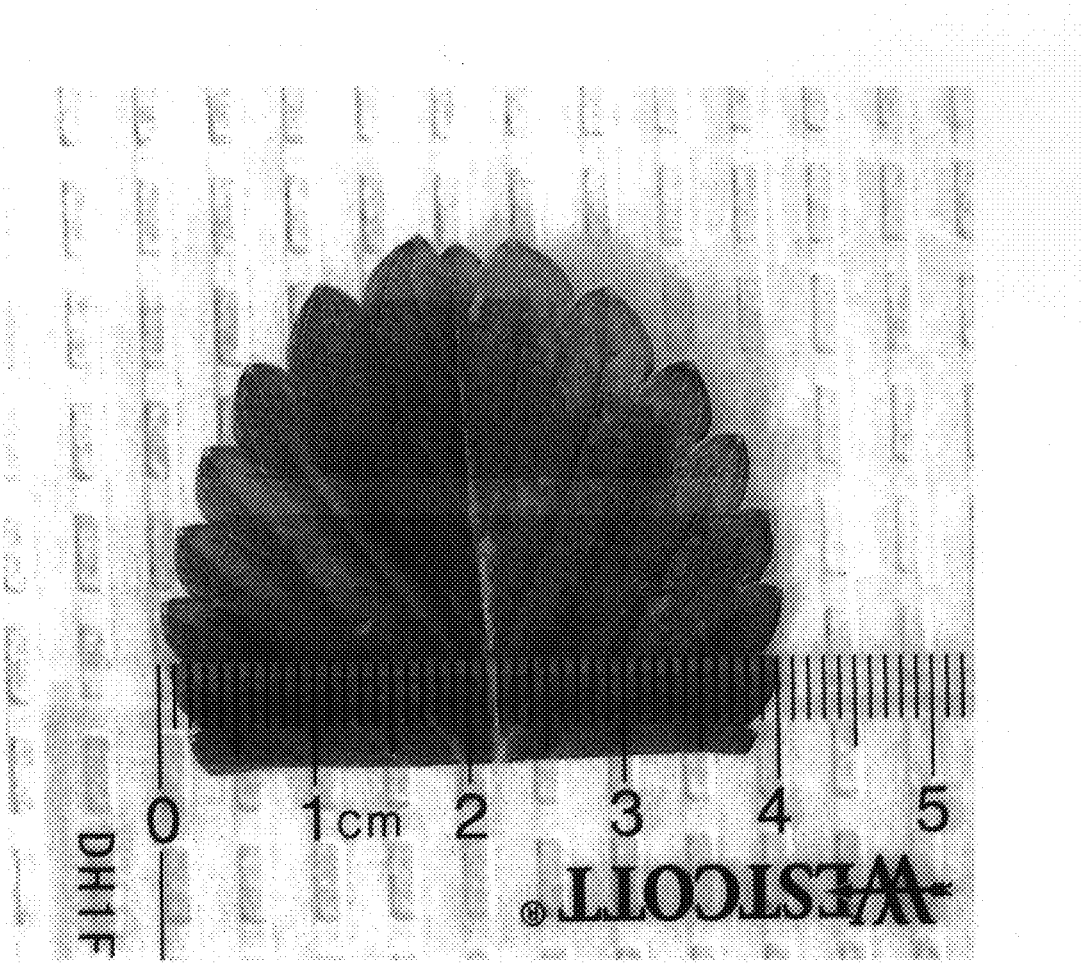
Figure 4C:
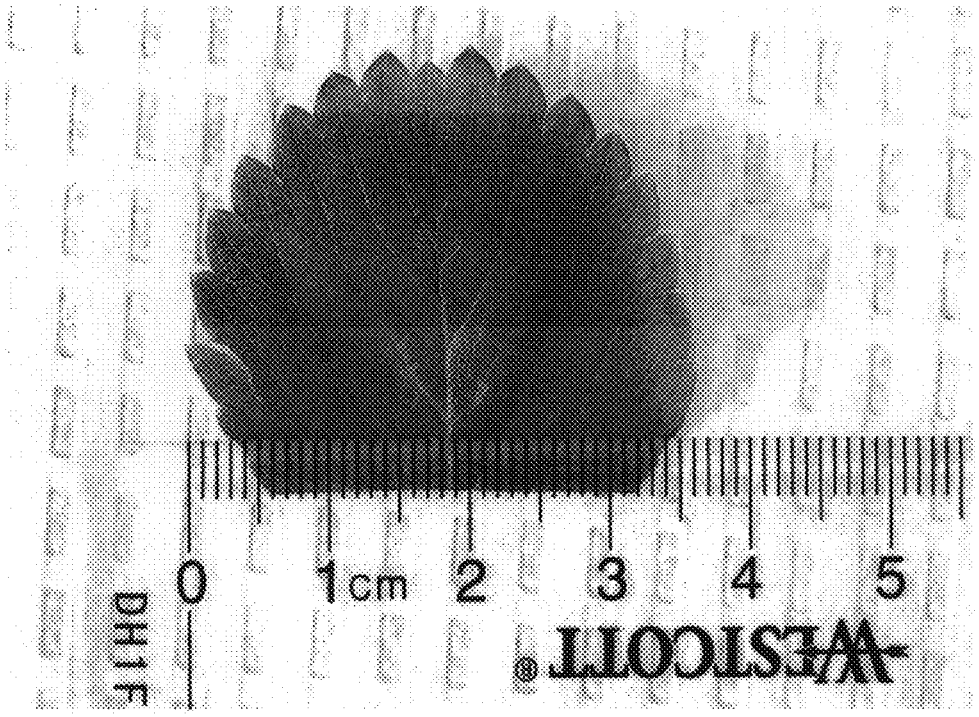

FIGS. 4A-C show leaf margin serrations for 'Archer' (FIG. 4A), 'Jewel' (FIG. 4B), and 'L'Amour' (FIG. 4C).

DETAILED BOTANICAL DESCRIPTION

The present invention relates to a new and distinct June-bearing (short day responsive) strawberry plant designated as 'Archer'. The plant is botanically known as *Fragaria* x *ananassa* Duch.

The following description of 'Archer', unless otherwise noted, is based on observations taken during the 2016 growing season in Geneva, N.Y. These measurements and ratings were taken from plants planted in May 2015. The age of the planting was approximately 13 months and in its first harvest season. Yield observations and fruit quality characteristics are averaged from data collected during the 2013 and 2014 production seasons. The characteristics of the new plant may vary in detail, depending upon variations in environmental factors (temperature, rainfall, humidity, and light intensity). Where noted, color terminology follows The Royal Horticultural Society Colour Chart, London.

COMPARATIVE FRUIT CHARACTERISTICS

Tables 1-4 provide comparative characteristics of 'Archer' fruit, fruit production, and fruit quality characteristics. Fruit characteristics are taken from the first harvest season.

TABLE 1

Fruit characteristics: Yield

| Cultivar (kg per ha) | 2013 | 2014 | Average |
|---|---|---|---|
| 'Archer' | 12,190 | 18,100 | 15,150 |
| 'Clancy' | 9,040 | 10,560 | 9,800 |
| 'Ovation' | 9,830 | 12,680 | 11,260 |

TABLE 1-continued

Fruit characteristics: Yield

| Cultivar (kg per ha) | 2013 | 2014 | Average |
|---|---|---|---|
| 'Jewel' | 9,380 | 12,680 | 11,030 |
| 'Seneca' | 17,040 | 11,200 | 14,120 |

Total fruit yield of 'Archer' and similar varieties from 2 separate trials, one harvested in 2013 and one in 2014 in Geneva, NY. Fruit was harvested in June of each year. The plants of 'Archer' and the other varieties were grown in a cooperating commercial nursery in Hartford, MI or South Deerfield, Mass. and planted in May prior to the first harvest year for both trials.

TABLE 2

Fruit characteristics: Weight

| Cultivar (g per berry) | 2013 | 2014 | Average |
|---|---|---|---|
| 'Archer' | 15.3 | 13.3 | 14.3 |
| 'Clancy' | 14.7 | 12.8 | 13.8 |
| 'Ovation' | 11.8 | 11.3 | 11.6 |
| 'Jewel' | 13.9 | 10.9 | 12.4 |
| 'Seneca' | 12.9 | 12.5 | 12.7 |

Average fruit weight of 'Archer' and similar varieties from 2 separate trials, one harvested in 2013 and one in 2014 in Geneva, NY. Fruit was harvested in June in each year. The plants of Archer' and the other varieties were grown in a cooperating commercial nursery in Hartford, MI or South Deerfield, Mass. and planted in May prior to the first harvest year for both trials.

TABLE 3

Fruit characteristics: Color and Dimensions

| Character | 'Archer' | 'L'Amour' | 'Jewel' | 'Clancy' |
|---|---|---|---|---|
| RHS Exterior Color Mature Fruit | red 45A | red 46B | red 44A | red 46A |
| Fruit Length mean (cm) | 4.65 | 4.22 | 3.46 | 3.07 |
| Fruit Width mean (cm)[1] | 4.35 | 3.62 | 3.61 | 3.59 |
| Fruit Length/ Width Ratio | 1.07 | 1.20 | 1.05 | 0.86 |
| No. Sepals/ Berry | 14.0 | 11.0 | 12.4 | 11.9 |

Comparison of mature secondary fruit characteristics of 'Archer' with standards grown in Geneva, NY

[1]Width is measured across the widest part of the berry, typically across the shoulders.

TABLE 4

Fruit characteristics: Chemical Qualities

| Character | 'Archer' | 'L'Amour' | 'Jewel' | 'Clancy' |
|---|---|---|---|---|
| Soluble solids[1,2] | 8.17 | 8.91 | 7.80 | 9.02 |
| Titratable acidity[2,3] | 7.55 | 8.93 | 6.61 | 8.93 |
| Juice pH[2] | 3.23 | 3.68 | 3.44 | 3.54 |

Comparison of soluble solids (% Brix), titratable acidity, and juice pH of 'Archer' with standards grown in Geneva, NY.

[1]Soluble solids is estimated from % Brix with % Brix being an indirect measurement of the sugar content in the fruit.

[2]Averaged from 3 samples on 3 dates during the harvest season.

[3]g per L equivalents of citric acid.

Detailed fruit characteristics of 'archer':

*Ratio of length/width*.—Longer than broad.

*Size*.—Large.

*Aroma*.—High.

*Predominant shape*.—Broad conical.

*Difference in shapes between primary and secondary fruit*.—Low to moderate.
*Band without achenes*.—Intermediate width.
*Color of mature fruit*.—Bright to dark red.
*Evenness of color*.—Usually even, but can be uneven with high ripening temperatures.
*Glossiness*.—Moderate.
*Insertion of achenes*.—Level to slightly recessed from surface.
*Attitude of the calyx segments*.—Somewhat reflexed.
*Size of calyx in relation to fruit diameter*.—Generally smaller.
*Adherence of calyx* (*when fully ripe*).—Strong.
*Firmness of skin*.—Moderate.
*Firmness of flesh*.—Moderately firm.
*Color of flesh*.—Medium red with lighter inner ring (orange-red 34B to 33C).
*Distribution of red color of the flesh*.—Marginal through central with pale orange-red ring.
*Hollow center*.—Strongly expressed in primary and secondary fruit. The hollow center is longer than it is wide. The mean hollow center size in primary fruit is 20.4 mm long×10.1 mm wide with a length to width ratio of 2.02 in fruit 25 to 35 g weight. For secondary fruit, the mean hollow center size is 15.8 mm long×6.8 mm wide with a length to width ratio of 2.32 in fruit 14 to 20 g weight. The hollow center is proportionally larger in larger fruit. Fruit larger than 35 g would be expected to have a larger cavity with a similar length to width ratio.
*Seed color*.—Medium yellow-green to occasionally red on sun exposed side (yellow-green 153D to orange-red 34B).
*Time of flowering* (*50% of plants at first flower*).—Early to medium.
*Time of ripening* (*50% of plants with first ripe fruit*).—Early to medium.
*Type of bearing*.—Fully short day responsive.

COMPARATIVE PLANT CHARACTERISTICS

Table 5 provides comparative 'Archer' plant characteristics. Plant characteristics are taken from a fully mature mid season plant.

TABLE 5

Plant characteristics: Comparisons

| Character | 'Archer' | 'L'Amour' | 'Jewel' | 'Clancy' |
|---|---|---|---|---|
| Plant Height (mean cm) | 30.4 | 31.9 | 27.3 | 26.1 |
| Vigor[1] | 8.5 | 8.3 | 5.0 | 7.0 |
| Canopy density[1] | 8.5 | 7.7 | 7.0 | 7.5 |

Comparison of plant characteristics of 'Archer', with standards grown in Geneva, NY
[1]Rated on a scale of 1-9 (9 being more vigorous or dense) in mature replicated plots.

Detailed plant characteristics of 'archer':
*Size*.—Large.
*Habit*.—Moderately upright.
*Density*.—High.
*Vigor*.—Strong.

COMPARATIVE FOLIAGE CHARACTERISTICS

Table 6 provides comparative 'Archer' foliage characteristics. Foliage characteristics are taken from a fully mature tri-foliate during mid season.

TABLE 6

Foliage characteristics: Comparisons

| Character | 'Archer' | 'L'Amour' | 'Jewel' |
|---|---|---|---|
| RHS Color (upper surface) | green 143B | green 137A | green 138A |
| RHS Color (lower surface) | yellow-green 146C | green 139C | green 137D |
| Terminal Leaflet Length mean (cm) | 8.8 | 8.4 | 7.5 |
| Terminal Leaflet Width mean (cm) | 8.3 | 8.5 | 7.6 |
| Terminal Leaflet ratio (L/W) | 1.07 | 0.99 | 0.99 |
| Petiole Length mean (cm) | 24.3 | 22.8 | 19.9 |
| Serrations/Leaf | 32.0 | 22.3 | 18.3 |
| Stipule Length mean (cm) | 2.7 | 3.5 | 3.0 |
| Stipule Width mean (cm) | 0.4 | 0.8 | 0.8 |

Comparison of leaf characteristics of 'Archer' to standards grown in Geneva, NY

Detailed foliage characteristics of 'archer':
*Color of upper surface*.—Dark green.
*Color of under side*.—Medium to light green with yellow undertone.
*Shape in cross section*.—Slightly concave.
*Interveinal blistering*.—Moderate to heavy.
*Glossiness*.—Moderate.
*Number of leaflets/leaf*.—Generally three with four or five present but uncommon.

Terminal leaflet:
*Size*.—Large.
*Length/width ratio*.—Longer than broad.
*Shape of base*.—Broadly cuneate, often uneven.
*Shape serrations*.—Mucronate.

Petiole:
*Pubescence density*.—High.
*Stipule color*.—Light to medium yellow-green (yellow-green N144C).
*Anthocyanin coloration of stipule*.—Common on young leaves.
*Attitude of hairs*.—Generally toward petiole base.
*Size of bract leaflets*.—Small.
*Frequency of bract leaflets*.—Occur rarely on the petioles.

COMPARATIVE FLOWER AND INFLORESCENCE CHARACTERISTICS

Table 7 provides comparative 'Archer' inflorescence and flower characteristics. Inflorescence characteristics are taken from a fully mature plant during full bloom. Flower characteristics are taken from a secondary flower during mid season at full maturity.

TABLE 7

Flower and Inflorescence Characteristics: Comparisons

| Character | 'Archer' | 'L'Amour' | 'Jewel' |
|---|---|---|---|
| Fruiting Truss Length (mean cm)[1] | 25.6 | 32.3 | 20.9 |
| Corolla Diameter (mean mm) | 34 | 36 | 31 |
| Calyx Diameter (mean mm) | 32 | 33 | 34 |

TABLE 7-continued

| Flower and Inflorescence Characteristics: Comparisons | | | |
|---|---|---|---|
| Character | 'Archer' | 'L'Amour' | 'Jewel' |
| Petal Length (mean mm) | 14.8 | 15.4 | 14.0 |
| Petal Width | 13.7 | 13.6 | 13.3 |
| Petal L/W Ratio | 1.08 | 1.13 | 1.09 |
| Petals/Flower (mean) | 5.2 | 5.1 | 6.3 |
| Sepals/Flower (mean) | 10.0 | 11.0 | 12.4 |

Comparison of inflorescence and secondary flower characteristics of 'Archer' with standards grown in Geneva, NY
[1]As measured from the base of the primary peduncle where it attaches to the crown of the plant to the furthest berry.

Detailed inflorescence characteristics of 'archer':

*Position relative to foliage*.—Even to below.

*Fruiting truss length*.—Medium.

*Peduncle bract*.—Commonly large single.

Detailed flower characteristics of 'archer':

*Color*.—White (white 155C).

*Size*.—Medium to large.

*Size of calyx relative to corolla*.—Equal to smaller.

*Relative position of petals*.—Slight overlap when first fully open.

*Petal length/width ratio*.—Longer than broad.

*Petal shape*.—Obovate.

The varieties which are believed to most closely resemble 'Archer' are 'Clancy' (U.S. Plant Pat. No. 16,481), 'L'Amour' (U.S. Plant Pat. No. 16,480), and 'Jewel' (U.S. Plant Pat. No. 5,897).

In comparison to the similar plant 'Clancy', 'Archer' differs by the following characteristics. The plant of 'Archer' is taller with a more spreading in growth habit and greater vigor. The fruit of 'Archer' is larger than that of 'Clancy' with a more reflexed calyx. The fruit skin and flesh color of 'Archer' is lighter red than that of 'Clancy'. The yield of 'Archer' is larger than that of 'Clancy'. The fruit of 'Archer' has lower soluble solids (% Brix) and lower titratable acids than that of 'Clancy' with lower juice pH. The harvest season of 'Archer' is earlier than that of 'Clancy' and more extended in duration.

In comparison to the similar plant 'L'Amour', 'Archer' differs by the following combination of characteristics. The plant of 'Archer' is shorter and broader than 'L'Amour'. The terminal leaflets are slightly wider and shorter in length giving them a greater length to width ratio and a broadly elliptical to obovate shape. The stipules of 'Archer' are shorter and less wide than those of 'L'Amour' and more commonly pigmented, especially on young petioles. The fruit of 'Archer' is larger in size than 'L'Amour' with a broader cross section resulting in a lower length to width ratio. The fruit of 'Archer' has lower average soluble solids, lower titratable acids, and lower juice pH than 'L'Amour'. The flowering trusses of 'Archer' are shorter than those of 'L'Amour'. The flowers of 'Archer' are larger in diameter than the flowers of 'L'Amour' with a lesser petal length to width ratio than 'L'Amour'. The harvest season for 'Archer' is more extended than that of 'L'Amour'.

In comparison to the similar plant 'Jewel', 'Archer' differs by the following combination of characteristics. The plant of 'Archer' is more vigorous and is broader and taller than 'Jewel'. The foliage is wider and longer in 'Archer' compared to 'Jewel'. The stipules of 'Archer' are shorter and less broad than those of 'Jewel'. The fruit of 'Archer' is darker red in color than 'Jewel' with a more reflexed calyx. The fruit of 'Archer' has higher soluble solids, higher titratable acidity, and lower juice pH than that of 'Jewel'. The fruit of 'Archer' is larger than that of 'Jewel' with a prominent cavity in primary and secondary fruit. The fruiting trusses of 'Archer' are longer in overall length than those of 'Jewel'.

Test plantings in various locations in New York, Illinois, Minnesota, and Michigan have shown this plant to be widely adapted to differing soil and climactic conditions. It has shown cold hardiness typical to strawberries in a matted row system when covered with straw in the winter, which is standard procedure for this growing region. Fruit of the new plant ripens similar to its parent 'L'Amour' (U.S. Plant Pat. No. 16,480) and before its parent NY1786.

The new plant is primarily adapted to the climate and growing conditions of west central NY, the upper mid-western U.S, the Mid-Atlantic States, and southeastern Canada. This region provides the necessary winter temperatures required for it to produce a strong vigorous plant and to produce fruit in the summer harvest season from May to July, depending on location.

'Archer' is known to be moderately resistant to the two-spotted spider mite and susceptible to aphids and flower thrips. It is tolerant to leaf spot, leaf blight, and leaf scorch. It is moderately susceptible to foliar powdery mildew in mid-summer. The susceptibility of the new plant to any of the virus complexes of NY has not been determined.

What is claimed:

1. A new and distinct cultivar of strawberry plant named 'Archer' as herein described and illustrated by the characteristics set forth above.

* * * * *